(12) United States Patent
Nolan

(10) Patent No.: US 6,605,640 B2
(45) Date of Patent: Aug. 12, 2003

(54) METHOD OF TREATING CERTAIN EYE DISEASES

(76) Inventor: Gerard M. Nolan, P.O. Box 827, Ave., Farmington, CT (US) 06032

( * ) Notice: Subject to any disclaimer, the term of this patent is extended or adjusted under 35 U.S.C. 154(b) by 0 days.

(21) Appl. No.: 09/773,878

(22) Filed: Jan. 31, 2001

(65) Prior Publication Data

US 2002/0103167 A1 Aug. 1, 2002

(51) Int. Cl.[7] ............................................. A61K 31/205
(52) U.S. Cl. ...................... 514/556; 514/912; 424/669
(58) Field of Search ................................. 514/556, 912; 424/669

(56) References Cited

U.S. PATENT DOCUMENTS

| 5,288,735 A | 2/1994 | Trager et al. ................ 514/363 |
| 6,273,092 B1 | 8/2001 | Nolan ........................ 128/898 |
| 6,313,155 B1 | 11/2001 | Sponsel | |

OTHER PUBLICATIONS

Adams, Chromatic and Luminosity Processing in Retinal Disease, American Journal of Optometry & Physiological Optics; Dec. 1982; vol. 59 (12): 954–960.
Bowman, The Clinical Assessment of Colour Discrimination in Senile Macular Degeneration, Acta Ophthalmologica, 1980 vol. 58 (3): 337–346.
Bowman, The Relationship Between Color Discrimination and Visual Acuity in Senile Macular Degeneration, American Journal of Optometry, Mar. 1980; vol. 57 (3): 145–148.
Bresnick et al., Autosomal Dominantly Inherited Macular Dystrophy with Preferential Short–Wavelength Sensitive Cone Involvement, American Journal of Ophthalmology, Sep. 15, 1989; 108: 265–276.
Cheng et al., Visual Losses in Early Age–Related Maculopathy, Optometry and Vision Science, Feb. 1993; vol. 70 (2): 89–96.

Chu, et al., Clinical Studies of Color Vision with Gunkel's Chromagraph, Arch Ophthalmol Aug. 1983; vol. 101: 1232–1235.
Fishman, et al., Color Vision Defects in Retinitis Pigmentosa, Annals of Ophthalmology, May 1981; 13 (5): 609–618.
Zrenner, et al., Cone Function and Cone Interaction in Hereditary Degenerations of the Central Retina, Documents Ophthalmologica, Jan. 31, 1986; vol. 62 (1) : 5–12.
Holz, et al., Colour Contrast Sensitivity in Patients with Age–Related Bruch's Membrane Changes, German J. Ophthalmol Nov. 1995; vol. 4 : 336–341.
Kellner, et al.; Hereditary Mascular Dystrophies, Ophthalmologe 1998, Sep. 1995; vol. 9: 597–601 (Summary in English).
Mantyjarvi et al., Color Vision in Stargardt's Disease, International Ophthalmology Nov. 1992; 16 (6): 423–428.
Minato, Color Vision Defects of Macular Diseases; Nippon Ganka Gakkai Zasshi; ACTA Soc. Ophthalmol Japan; Apr. 1991; vol. 95: 354–362 (Abstract in English).
Smith, et al., Color Matching and the Stiles–Crawford Effect in Observers with Early Age–Related Macular Changes, J Opt Soc Am A Dec. 1988; vol. 5 (12) : 2113–2121.
Swanson, et al., Color Matches in Diseased Eyes with Good Acuity: Detection of Deficits in Cone Optical Density and in Chromatic Discrimination, J Opt Soc Am A Oct. 1995; vol. 12 (10); 2230–2236.

*Primary Examiner*—Zohreh Fay
(74) *Attorney, Agent, or Firm*—Nanda P. B. A. Kumar; William J. McNichol, Jr.; ReedSmith LLP

(57) ABSTRACT

The present invention is directed to methods for treating diminished visual acuity in a human patient who has been diagnosed as suffering from a disease or disorder of the posterior region of the eye. These involve topical application to the eye, an amount of acetylcholine esterase inhibitor containing composition is carried out so that it is sufficient to provide a therapeutic benefit to alleviate the diminished visual acuity in the human patient. The composition is administered at bedtime after an eye straining work for about 20 minutes.

47 Claims, 7 Drawing Sheets

METHOD OF TREATING CERTAIN EYE DISEASES

FIELD OF THE INVENTION

The present invention relates to a newly identified pharmacological treatment to treat age related diseases or disorders of the posterior segment of the eye. Specifically, the invention provides methods for restoring or alleviating visual acuity affected by retinal vascular diseases and choroidal vascular diseases and certain hereditary eye diseases by topical administration of acetylcholine esterase inhibitors.

BACKGROUND OF THE INVENTION

A diminished visual acuity or total loss of vision may result from a number of eye diseases or disorders caused by dysfunction of tissues or structures in the anterior region of the eye and/or posterior region of the eye. The eye is divided anatomically into an anterior and posterior segment. The anterior segment includes the cornea, anterior chamber, iris and ciliary body (anterior choroid), posterior chamber and crystalline lens. The posterior seqment includes the retina with optic nerve, choroid (posterior choroid) and vitreous. Some of the examples of eye disorders resulting from the pathologic conditions of structures in the anterior segment of the eye are dry eye syndrome, keratitis or corneal dystrophy, cataracts, and glaucoma. The disease or disorders of the posterior segment of the eye in general are retinal or choroidal vascular diseases or hereditary diseases such as Lebers Congenital Amaurosis. The posterior portion of the eyeball supports the retina, choroid and associated tissues.

So far certain treatments, including the topical application of acetylcholine esterase (ACHE) inhibitor, have been used with some success to treat ophthalmic disorders caused by dysfunction of eye muscles in the anterior region of the eye. Acetylcholine, when working on the eye or other smooth muscles of the body is regulated by the natural cholinesterase enzyme which breaks down acetylcholine and thus turns off its parasympathetic effect on muscles. The effect of acetylcholine on the muscles of the eye could be increased either by adding an acetylcholine like drug such as pilocarpine, or by blocking the breakdown of acetylcholine with an AChE drug which inhibits the natural cholinesterase (e.g., a cholinesterase inhibitor). However, the administration of acetylcholine (pilocarpine) results in the side effect of nearsightedness, thus acetylcholine treatment to correct presbyopia has not been effective.

A diminished visual activity may result due to pathologic conditions of tissues or structures located n the anterior segment of the eye or in the posterior region of the eye. Age related macular degeneration (AMD) is one of the specific diseases associated with the posterior portion of the eyeball and is the leading cause of blindness among older people. AMD results in damage to the macula, a small circular area in the center of the retina. Because the macular is the area which enables one to discern small details and to read or drive, its deterioration may bring about diminished visual acuity and even blindness. The retina contains two forms of light receiving cells, rods and cones, that change light into electrical signals. The brain then converts these signals into the images that we see. The macula is rich in cone cells, which give us our central vision. People with AMD suffer deterioration of central vision but usually retain peripheral sight.

There are several types of AMD. The "dry" (non-exudative) type accounts for about 90% of AMD cases. The wet (exudative) form afflicts only about 10% of AMD patients. However, the wet form is a more serious disease than the dry form and is responsible for about 90% of the instances of profound visual loss resulting from the disease. Wet AMD often starts abruptly with the development of tiny, abnormal, leaky blood vessels termed CNVs (chorodial new vessels), directly under the macula. In most patients, this leads to scarring and severe central vision loss, including distortion, blind spots, and functional blindness.

Signs of AMD such as drusen, which are abnormal yellow deposits under the retina, can be present even in patient with normal vision. Drusen look like specks of yellowish material under the retina. They are deposits of extracellular material that accumulate between retinal pigment epithelium (RPE) and Bruch's Membrane. The RPE is a specialized cell layer that ingests used-up outer tips of the rod and cone cells and provides them with essential nutrients (e.g. vitamin A derivatives). Bruch's membrane is a noncellular structure (made mostly of collagen) that separates the RPE from the choroidal circulation below. The choroidal circulation provides the blood supply to the rods, cones and RPE cells. A few small drusen normally form in the human eye, usually after age 40. AMD, in contrast, is almost always associated with a build-up of additional drusen. Drusen occur in two forms. Hard drusen are small, solid deposits that apparently do no harm when present in small numbers. Soft drusen are larger and may have indistinct borders. As soft drusen build up between the RPE and Bruch's membrane, they lift up the RPE and force the two layers apart.

Drusen develop long before the abnormal vessels of wet AMD. Three characteristics of soft drusen are risk factors for developing CNV: The presence of five or more drusen deposits; drusen size greater than 63 micrometers (about the thickness of a human hair); and, the clumping of the drusen deposits. Some evidence suggests soft drusen are instrumental in the spread of abnormal vessels, but whether they stimulate vessel growth (angiogenesis) or simply provide space for them by lifting up the RPE remains unclear.

Two networks of blood vessels nourish the retina, one located on the retinal surface and the other located deep in the retina, external to Bruch's membrane. The abnormal vessels of AMD originate in the lower network of vessels, called the choroidal circulation. These vessels make their way through Bruch's membrane and spread out under the RPE. Blood and fluids leak from them and cause the photoreceptor cells to degenerate and the macula to detach from the cells under it.

Slightly blurred or distorted vision is the most common early symptom of AMD. Visual loss with dry AMD usually progresses slowly while visual loss with wet AMD proceeds more rapidly and may occur over days or weeks. Patients who have wet AMD in one eye are at increased risk of developing CNVs in the other eye. The magnitude of the risk varies, depending on the appearance of the second eye. The risk is greater in eyes with numerous large drusen, with abnormal pigment changes in the macula, and in patients with a history of high blood pressure.

Presently, there are no effective treatments available for visually disabling retinal vascular disease or choroidal vascular disease such as diabetic retinopathy and age related macular degeneration (AMD). The therapeutic strategies for treating diminished or loss of vision caused by the vascular eye diseases vary. Laser photocoagulation is the first effective treatment found for wet AMD. The laser destroys abnormal blood vessels beneath the retinal and seals leaky areas but also destroys the overlying retina. This treatment can inhibit wet AMD's progression, but it cannot restore lost vision and the disease often progresses despite laser therapy. The use of the drug Visudyne (veteporfin) is another approach to treat AMD. This drug belongs to a class of drugs used in photodynamic therapy (PDT), a technique in which light-activated dyes destroy tissue. After an injection, the light-sensitive drug tends to localize in the new choroidal vessels. A low-intensity laser is then focused on the dye-containing CNVs, triggering a chemical reaction that destroys the abnormal vessels. The drug can stabilize vision for a time and slow retinal damage. Other PDT drugs for AMD are currently in clinical testing. However, even with the availability of PDT and conventional laser treatment, patients with the vascular diseases of the eye still have no known effective treatment option and remain vulnerable to sustaining permanent damage to the retinal cells.

The other retinal or choroidal vascular diseases include but not limited to macular cyst, macular hole, solar retinopathy, diabetic retinopathy, branch retinal vein occlusion.

Hitherto it has not been known that a particular regimen of the topical administration of AChE inhibitor can arrest or alleviate the deterioration of vision associated with retinal or choroidal disorders resulting from the pathological conditions of tissues or structures located in the posterior region of the eye.

SUMMARY OF THE INVENTION

In accordance with the present invention, various eye diseases or disorders of the posterior segment of the eye, especially those related to the retinal and choroidal vascular diseases, are treated by topical administration to the patient's affected eye of an amount of a acetylcholine esterase inhibitor in a concentration effective to increase visual acuity of the diseased eye without adverse effects. Therefore, this invention provides several advantages over prior art laser therapy based methods employed for alleviating visual acuity in patients suffering from an eye disease in the posterior segment of the eye.

In a general aspect, A method of treating a human patient suffering from a retinal or choroidal vascular disease or hereditary retinal or choroidal disease, the method of topically administering to an eye affected with disease, an amount of a acetylcholine esterase inhibitor containing composition sufficient to provide a therapeutic benefit to alleviate the diminished visual acuity.

More specifically, a method of treating a human eye disease in the posterior segement of the eye is provided which involves the step of topically administering to an eye affected with the disease, an amount of a acetylcholine esterase inhibitor containing composition sufficient to provide a therapeutic benefit. The therapeutic benefit can be complete relief or cure from the eye disease or at least preventing the affected eye tissue from further deterioration (and stabilize the disease condition). The therapeutic benefit can also be the alleviation of the diminished visual acuity. The diseases in the posterior segment of the eye that can be treated by the present method included age related macular degeneration, macular cyst, macular hole, solar retinopathy, diabetic retinopathy, branch retinal vein occlusion and Lebers Congenital Amaurosis. The composition is administered at bedtime. In one embodiment, the inhibitor is (2-mercaptoethyl) trimethylammonium iodide O,O-diethyl phosphorothioate which is present at a concentration of about 0.001% to about 0.25%. The concentration of (2-mercaptoethyl) trimethylammonium iodide O,O-diethyl phosphorothioate can be about 0.0075%, or about 0.03%, or about 0.12%. The acetylcholine esterase inhibitor is contained in a pharmaceutically acceptable carrier buffer solution.

DETAILED DESCRIPTION OF THE INVENTION

Figure 1:
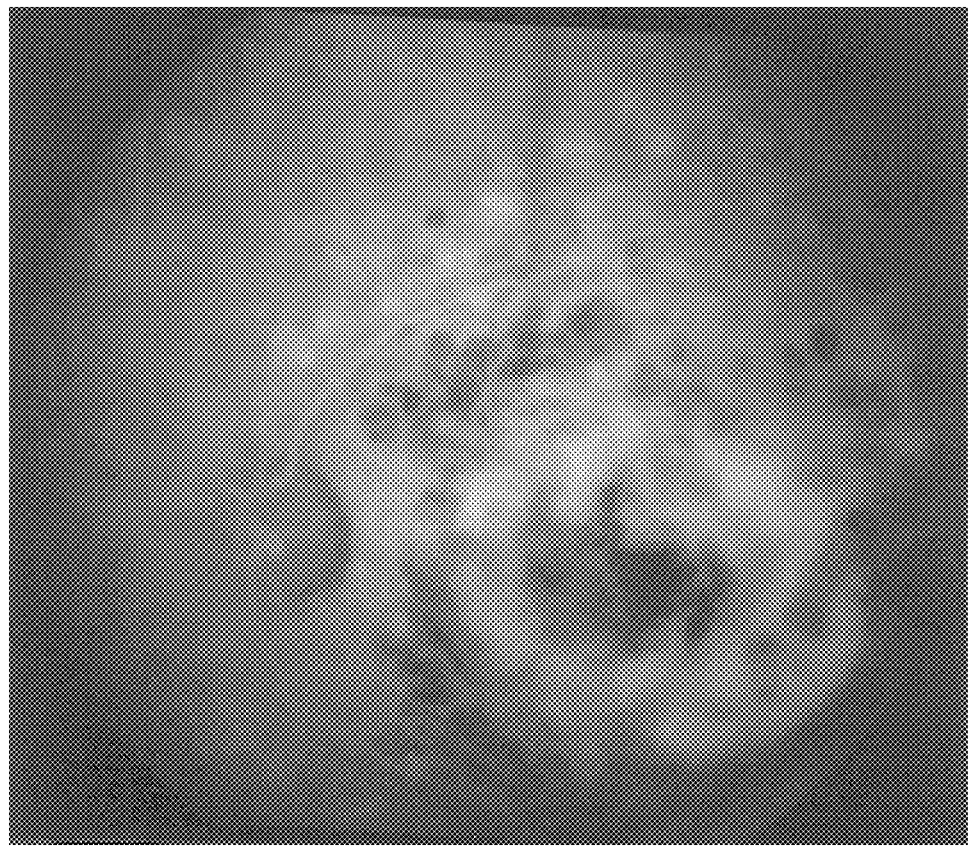
FIG. 1 is a photograph of an angiogram of a patient's eye who has been diagnosed as suffering from wet AMD.
Figure 2:
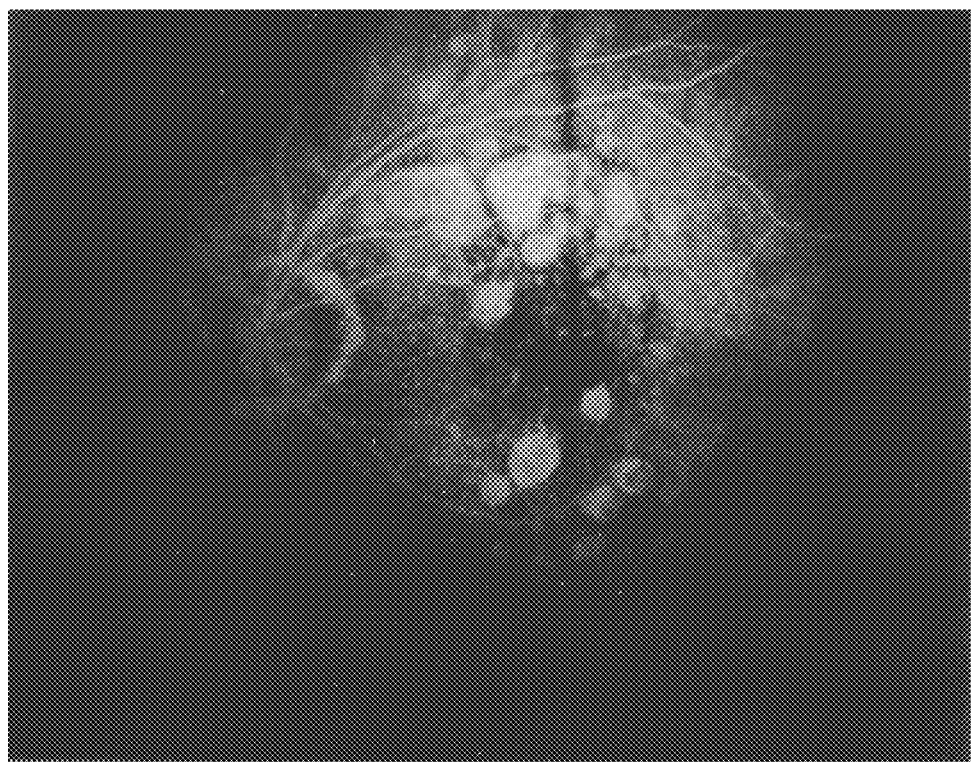
FIG. 2 is a photograph of an angiogram of a patient's eye who has been diagnosed as suffering from dry AMD.
Figure 3:
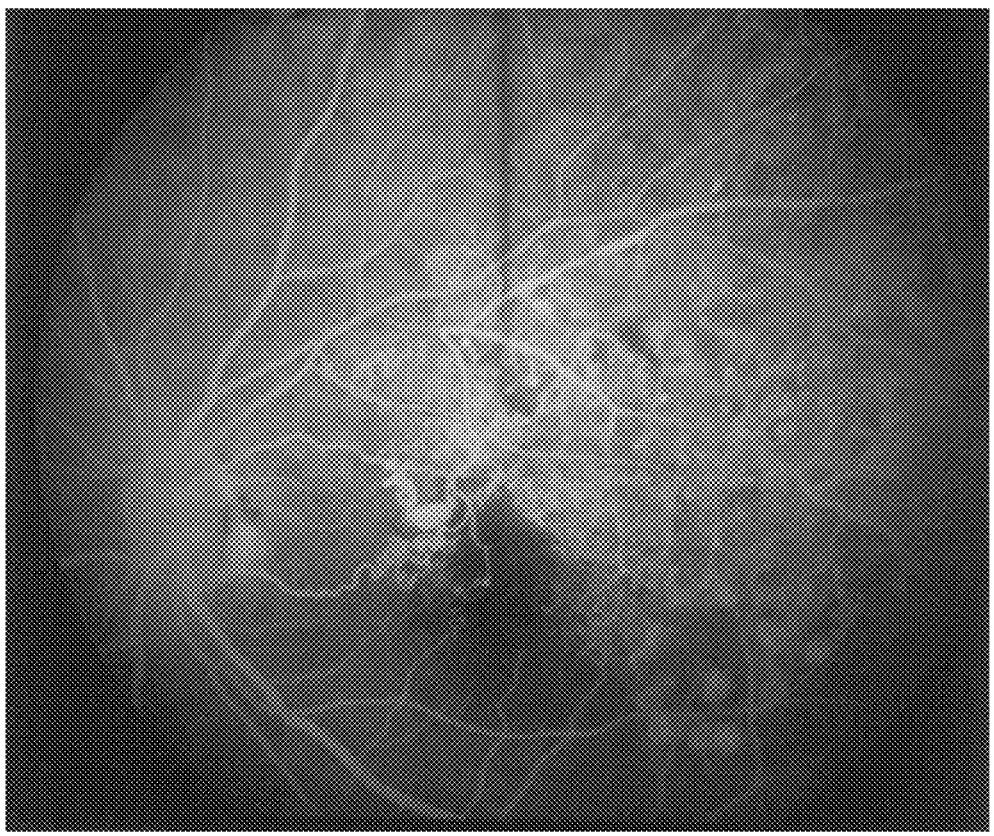
FIG. 3 is a photograph of an angiogram of a patient's eye who has been diagnosed as suffering from retinal vascular ocglusions.
Figure 4:
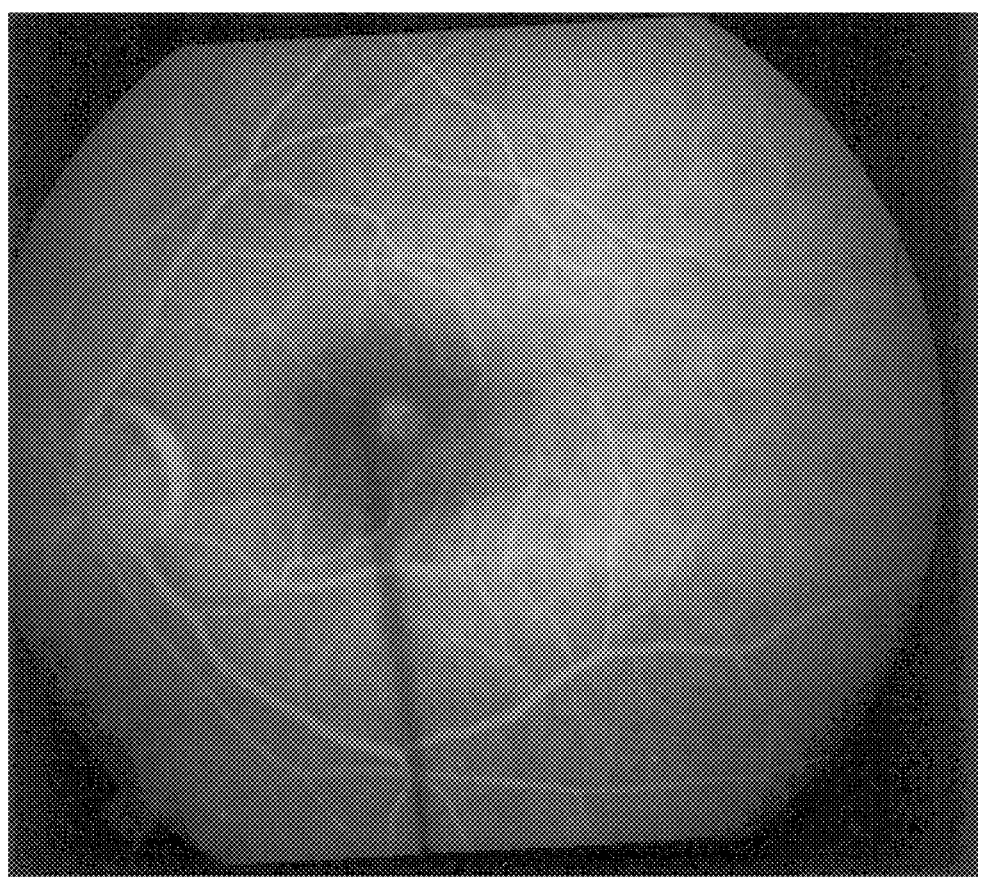
FIG. 4 is a photograph of an angiogram of a patient's eye who has been diagnosed as suffering from a macular hole.
Figure 5:
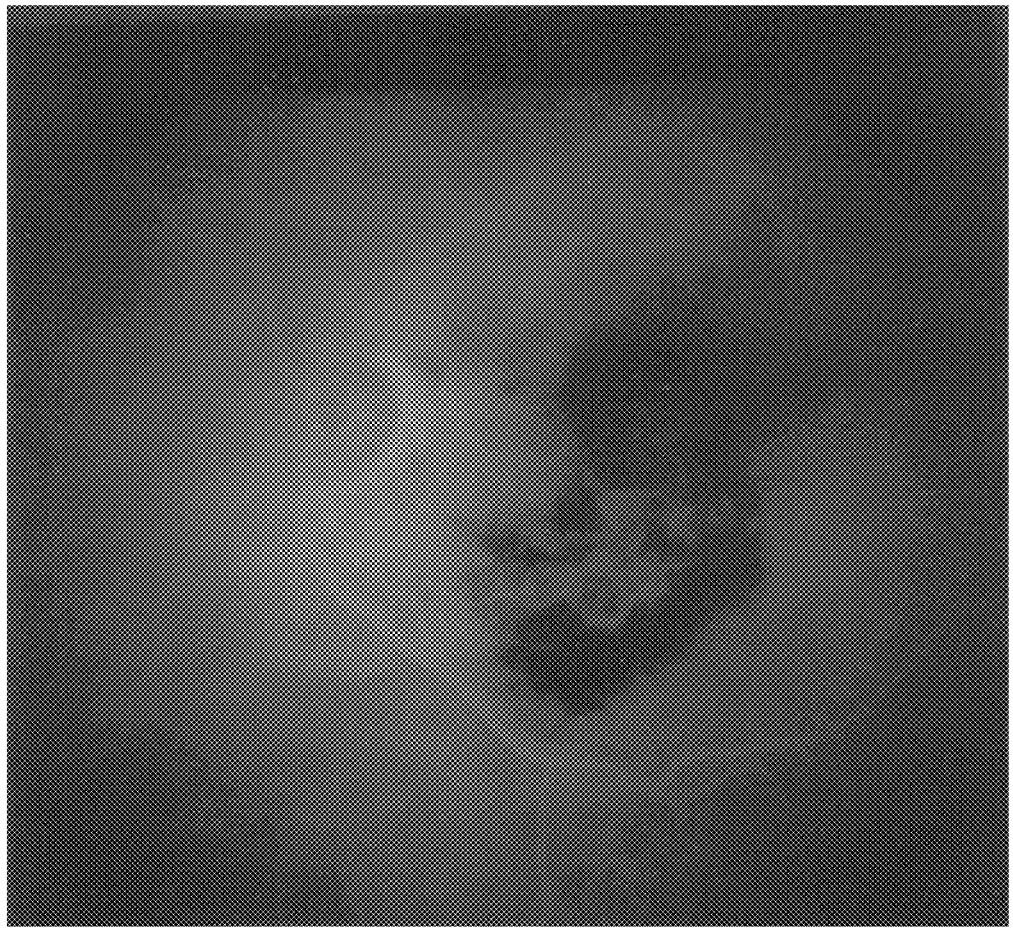
FIG. 5 is a photograph of an angiogram of a patient's eye who has been diagnosed as suffering from a Branch retinal vein occlusion.
Figure 6:
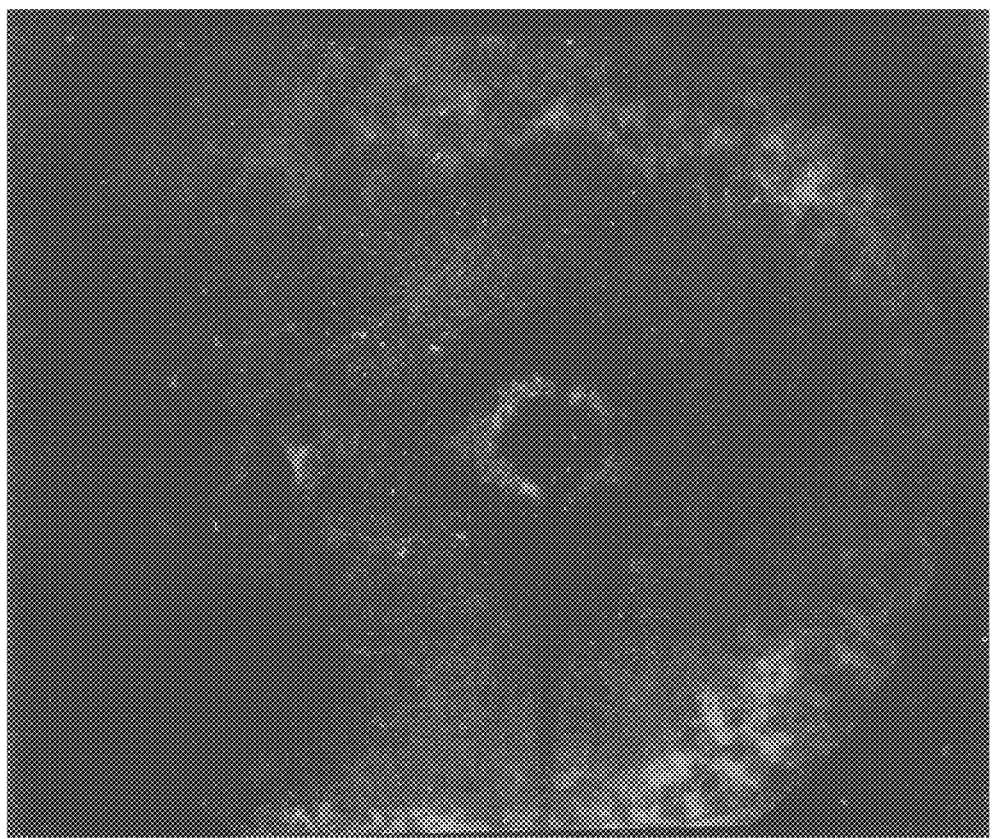
FIG. 6 is a photograph of an angiogram of a patient's eye who has been diagnosed as suffering from Lebers Congenital Amaurosis.
Figure 7:
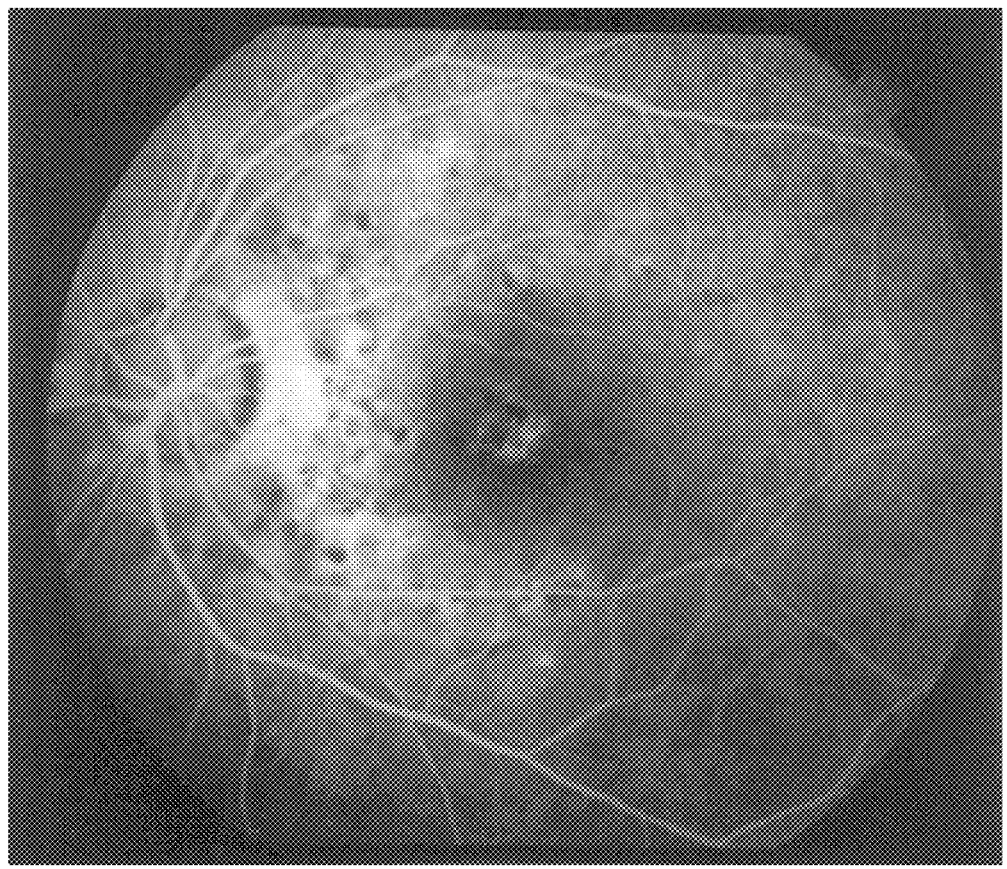
FIG. 7 is a photograph of an angiogram of a patient's eye who has been diagnosed as suffering from solar retinopathy.

The present invention provides methods for treating eye diseases such as retinal or choroidal vascular diseases and certain hereditary eye diseases associated with the pathological state of the tissues and structures in the posterior segment of the eye. The methods use the topical application of acetylcholine esterase inhibitors in very low concentrations but sufficient enough to effectively restore the visual acuity.

By practicing the method of the present invention, alleviation of diminished visual acuity due to, for example, macular cyst, macular hole, solar retinopathy, diabetic retinopathy, branch retinal vein occlusion and AMD can be achieved. By "restoration or alleviation of diminished visual acuity", it is meant that any significant improvement in vision of a patient suffering from blindness or poor vision.

These diseases in human patients are usually diagnosed by opthalmologistis or other physicians familiar with etiology of eye, by means of special photography of the retina. In a typical diagnostic procedure, flourecein angiography, the physician injects a fluorescein vegetable-base dye into a patient's blood. The patient's pupil is also dilated by administering pupil dilating drugs (mydriatic) to the eye. The physician then takes a series of photographs of the retina, using a light source at a particular excitation wavelength so that it causes any leakage of fluid of the drug from the patient's retinal and choroidal vasculature to emit fluorescent light at a different wavelength. The physician then analyzes the series of photographs of the retina to determine the presence and concentration of leakage. If present at abnormal levels as determined a physician skilled in this area, these abnormal levels of fluorescent leakage indicate the presence or onset of a particular retinal or choroid vascular disease.

By practicing the method of the present invention, the disease condition of the yea is at least stabilized without further deterioration of the tissues.

The structure, cellular anatomy physiology, biochemistry and other details of the eye are provided in various ophthalmological and medical school texts that focus specifically on the eye and diseases of the eye e.g. Dwanes Textbook of Ophthalmology, the American Academy of Ophthalmology Clinical Science Course, etc. The practicing physicians in this art can readily determine anatomical structures of a normal and diseased human eye whether the disease be in the anterior or posterior region of the eye ball. Once a human patient is diagnosed as suffering from a disease such as those described in the above paragraph, an amount of a acetylcholine esterase inhibitor containing composition sufficient to provide a therapeutic benefit is administered.

Acetylcholine esterase inhibitors are known to one skilled in the art. There are at least two ACHE inhibitor drugs currently approved for clinical use on the eye in the United States. They are (2-mercaptoethyl) trimethylammonium iodide O,O-diethyl phosphorothioate sold as PHOSPOHLINE IODIDE® (Wyeth-Ayerst, Philadelphia, Pa.), and physostigmine (also known as eserine) sold as ANTILIRIUM® (Forest Pharmaceuticals, St. Louis, Mo.). PHOSPHOLINE IODIDE is dispensed as eyedrops at a desired potency. PHOSPHOLINE IODIDE of various concentrations, such as for example 0.25%, 0.125%, 0.06% and 0.03% and a pharmaceutically acceptable sterile diluent to dilute the concentrated form of this drug are commercially available. PHOSPHOLINE IODIDE is currently used for glaucoma and accommodative esotropia. As such, PHOSPHOLINE IODIDE is not a preferred drug even to treat glaucoma and accommodative esotropia because of many adverse side effects caused by this drug when it is used in the current regimen of multiple times a day at high concentrations. Some of the side effects known to be caused by the currently recommended doses of this drug (for glaucoma at 0.12 and 0.25 BID) are iris cysts, cataract formation especially anterior subcapsular, posterior synechiae and elevated intraocular pressure.

In the new method, the cholinesterase inhibitor, such as phospholine iodide, administered in concentrations many fold more dilute than currently available pharmacological preparations, applied to the eye before sleep will achieve alleviation of the deteriorated or deteriorating vision with none of the unacceptable side effects of the usual pharmacological preparations and without the loss of peripheral vision. The effect of one administration of the inhibitor can last for many days. The present invention shows that the effective concentration of AChE inhibitor in the composition to treat diseases associated with the posterior region of the eye can be very low (for example, as low as at least 0.001% to about 0.0075% of PHOSPHOLINE IODIDE) to be effective. The invention discloses that such a concentration is extremely useful medically. Specifically, this lower dose range is especially useful in providing eye drugs that will contain a concentration of AChE inhibitor that is low enough to be both safe and effective. For example, application of a drop of 0.03% PHOSPHOLINE IODIDE followed by a drop of suitable diluent (e.g., artificial tear) is not incompatible with the drug.

The composition administered to the eye should have a pharmaceutically acceptable carrier and a selected AChE inhibitor suspended or dissolved in the carrier. The concentration of AChE inhibitor in the composition administered to the eye and the method of administration of the composition in accordance with this invention depends on the type of AChE inhibitor containing composition used for therapy. For example, preferred concentrations of PHOSPHOLINE IODIDE in the PHOSPHOLINE IODIDE containing composition are from about 0.25% to about 0.001%. More preferred PHOSPHOLINE IODIDE concentrations are from about 0.15% to about 0.005%. Most preferred PHOSPHOLINE IODIDE concentrations are about 0.12%, 0.03% and 0.0075%. It is preferred to apply PHOSPHOLINE IODIDE topically to the eyes in the form of eyedrops. Although it is preferred that these solutions with various concentrations of PHOSPHOLINE IODIDE are stored in a refrigerator, they an be stored at room temperature for about two months or even beyond two months without losing their efficacy to restore near vision in presbyopic patients.

A solution containing chlorobutanol (0.55%), mannitol (1.2%) boric acid (0.6%) and exsiccated sodium phosphate (0.026%) can be used as a carrier solution and/or as a diluent for PHOSPHOLINE IODIDE. While this solution is presently sold as a diluent in the kit containing PHOSPHOLINE IODIDE, other pharmaceutically acceptable carriers or excipients that are known to enhance membrane permeability and cellular uptake of the drug can be used as diluents with or without modification for application to the eye. Such carriers are known to one skilled in the art.

In a preferred embodiment of the invention, the AChE inhibitor is administered at bedtime. A single topical application of a given AChE inhibitor at bedtime can enhance visual acuity in the phakic emmetropic patients as well as in pseudophakic patients for a few days. For example, application of one to two drops of PHOSPHOLINE IODIDE of a selected concentration at bedtime can alleviate the diminished vision of the patients for at least five days. Preferably, the following steps are followed every time AChE inhibitor is applied to the patient. The first step is to read for about 30 minutes. The second step is to administer an AChE inhibitor of a selected concentration. The third step is to sleep. Without wishing to be bound by any theory or explanation, it is believed that the reading for about 30 minutes preconditions eye muscles and visual pathway to respond better to the AChE inhibitor treatments. It takes about 6 to 8 hours of sleep to notice the restoration. If one is awaken in the middle of sleep, the individual may notice partial effect but after 6 to 8 hours of sleep the effect will be maximized. By the term "bedtime" it is meant that the time when the patient goes to sleep for about 6 to 8 hours, regardless of whether it is during the day or night time. The composition is administered at bedtime, i.e., it is administered just before the patient goes to sleep for about 6 to 8 hours.

AChE inhibitor can be administered to the eye with the disease. It should be noted that the method of this invention can be successfully used to treat diminished visual acuity in phakic as well as pseudophakic patients. The method can also enhance visual acuity of an individual who has no iris. Of particular interest is that this method can be successfully used to treat patients with artificial and rigid intraocular lenses (IOL's). IOL's are inserted at the time of cataract surgery and in refractive procedures to make an individual emmetropic by clear lens extraction. Further, it should be noted that the diminished visual acuity can occasionally be alleviated also in contralateral eye (or untreated eye) to some degree.

Accordingly, by practicing the present invention, one can achieve a definite, measurable gain in visual acuity in patients with retinal vascular or choroidal vascular disease or other known diseases of posterior segment of the eye when administered with the acetylcholinesterase inhibitor, in the dilution and the manner outlined above. Increase in visual acuity can be measured by techniques well known to those skilled in the art. Although the mechanism of action is unknown, it is believed that a suitable dose of AChE inhibitor administered at bedtime may allow the eye to accumulate sufficient stockpiles of acetylcholine by inhibiting acetylcholine esterase activity in the eye and strengthen the eye muscles leading to the normal perfusion of the blood to the posterior region of the eyeball particularly choroid blood vessels. Retinal and choroidal function and health are dependant on normal perfusion of these tissues.

EXAMPLE

The example below is carried out using standard drug administration techniques, that are well known and routine to those of skill in the art, except where otherwise described in detail. The example is illustrative, but does not limit the invention. This example illustrates the alleviation of diminished visual acuity in humans suffering from diseases or disorders of the posterior segment of the eye by topical administration of an AChE inhibitor to the eye.

Treatment of Patients with Disorders in the Posterior Region of the Eye.

Twenty nine patients (34 eyes) were studied with ages 42 to 92. Etiology varied from diseases of the choroidal vasculature such as dry AMD and wet AMD, macular hole, Solar Retinopathy, Lebers Congential Amaurosis and retinal vascular diseases such as Diabetic Retinopathy with Maculopathy, and Retinal Vascular Occlusion. All of the patients studied showed restoration of vision. Patients included both phakic and pseudophakic. Medications were applied similarly at bedtime after about 20 minutes of reading once a week. Patients monitored their visions and if there was a regression of vision midweek, the dose was made twice weekly. A drop of PHOSPHOLINE IODIDE at a concentration of 0.03% with or without a drop of an artificial tear as a diluent was the regimen. Two patients stopped their medications and lost the effect (patient 5 and 9). One patients began using the medication in the morning and likewise lost the effect (patient 12). Another patient (patient 14) administered the drug at dinner time and lost the effect. These four patients had their visions restored on restarting the medications at bedtime after reading for about 20 minutes. The vision restoration is immediate and generally noticed on the first day or week of treatment. The medication was given unilaterally, that is to the diseased or more diseased eye. Most patients showed a contriction of the pupil in both eyes although the medication is given in only one eye. Pupil constriction is not necessary for vision improvement, as seen in patient 29 who is aniridic (no iris). Occasionally, patients noticed an improvement of vision also in the opposite or contralateral eye. That is, patients with bilateral disease, when the poorer of the two eyes is treated, the untreated better eye can show an effect of vision improvement. All patients were given pre treatment comprehensive examinations and had documented retinal and/or choroidal vascular disease by flourescein angiography.

Patient 1: This patient was pseudophakic and diagnosed as suffering from wet AMD. Prevision was counting fingers (CF), pinhole vision no help (PHNH). At one foot, vision was 1'/400. On day one, vision improved to 1'/100 or to 3'/400. At one week vision was 6'/400 and at two weeks 20'/300. At 8 weeks, distant vision was 20/400, 20/300 and near vision 20/70. At 3 months vision was 20/200–1.

Patient 2: This patient was pseudophakic and diagnosed as suffering from dry AMD. Prevision 20/40–2 PHNH. At one week 20/30 ph 20/25. At 8 weeks vision was 20/30–

Patient 3: This patient was pseudophakic and diagnosed as suffering from retinal vascular occlusions. Prevision CF PHNH 3'/300. At one week vision improved to 3'/70. At week two vision was 3'/25 or 6'/400 and near vision 20/70.

Patient 4: This patient was pseudophakic and diagnosed as suffering from dry AMD. Prevision 20/70– near vision 20/40. At one week vision improved to 20/50–1 near vision 20/25. At two weeks vision was 20/40–. At 4 weeks vision was 20/40–2, near vision 20/25.

Patient 5: This patient was pseudophakic and diagnosed as suffering from dry AMD and preretinal fibrosis. Prevision was 20/50–2. At one week vision was 20/40 PH 20/30– and at two week 20/30. At 8 weeks vision remains 20/30. At 3 months BK has stopped medusa for 10 days and vision was 20/40–3.

Patient 6: This patient was pseudophakic and diagnosed as suffering from dry AMD s/p laser for wet AMD. Prevision was 20/25+2. At one week vision 20/20–1. At week three vision was 20/20–1.

Patient 7: This patient was pseudophakic and diagnosed as suffering from early or pre AMD. Prevision was 20/30 +2. At one week vision was 20/25+1 and at two week 20/20. At week four vision was 20/15–1. At three months vision was 20/20–1, near vision 20/20.

Patient 8: This patient was phakic and diagnosed as suffering from dry AMD. Prevision was 20/25. At one week vision was 20/20. At week two vision was 20/15–1.

Patient 9: This patient was pseudophakic and diagnosed as suffering from dry AMD. Prevision was CF PHNH. At one week vision was 20/200. At two weeks CF the patient stopped taking medications. At week three on medications vision returned to 20/200. The patient admits to a marked improvement of peripheral. At six weeks vision was 20/200 and near vision 20/50.

Patient 10: This patient was phakic and diagnosed as suffering from macular holes both eyes. Best vision was right eye 20/100 PH 20/100+1, near 20/70, left eye 20/100–1 PHNH., near 20/70. At one week right 20/70– near 20/30, left 20/70–1 near 20/70. At three months vision was 20/70–2 near uncorrected 20/50–right (last drop right was one week), left was 20/70–1 with a near uncorrected 20/30 (last drop was last night). Binocular near vision was 20/25– and patient is reading for the first time five years+.

Patient 11: This patient was pseudophakic and diagnosed as suffering from diabetic retinopathy with maculopathy. Prevision was 20/70 PHNH near 20/50. At one week no effect. At two weeks vision 20/40–1 near 20/25. At six weeks vision remained stable at 20/40–1T.

Patient 12: This patient was pseudophakic and diagnosed as suffering from dry AND. Prevision was CF PHNH or 1'/400. At one week vision was 3/400, two weeks 6'/400 and at three weeks 20/300. For the next four weeks the patient began using drops in the am. At 8 weeks vision was CF PHNH, 1/400' snf and at 9 weeks 3/400. At 11 weeks vision was 6 feet/200.

Patient 13: This patient was pseudophakic and diagnosed as suffering from dry AMD. Prevision was 20/100–1 PHNH near vision was 20/40–. At week one vision was 20/50–1 and near vision 20/25.

Patient 14: This patient was pseudophakic and diagnosed as suffering from dry AMD. Prevision was 20/100 PHNH. At one week vision was 20/50. At two weeks, vision was 20/40–3. The patient began using drops at dinner time and lost effect although pupil was constricted at week four.

Patient 15: This patient was pseudophakic and diagnosed as suffering from wet AMD left eye and dry AMD right. Prevision was 20/40+ PHNH right and CF PHNH 1'/400 left. At week one, vision was 1/100– with noticeable increase in peripheral vision. The patient could read the time on his watch with the left eye. At week two, vision was 20/400+. (left eye) right eye at week one, vision was 20/30+1 and at week two, vision 20/20–.

Patient 16: This patient was pseudophakic and diagnosed as suffering from dry AMD right and wet AMD left. Prevision was 20/25− PHNH right and 20/200 PHNH. At one week vision was 20/20−2 right and 20/100 left. At one month vision was 20/20−2 and 20/200 left.

Patient 17: This patient was phakic and diagnosed as suffering from solar retinopathy from staring into the sun. Prevision was 20/30+ PHNH. At one week vision was 20/25. At three weeks vision was 20/25 (no eye drops for 8 days).

Patient 18: This patient was pseudophakic and diagnosed as suffering from BRVO (Branch Retinal Vein Occlusion). Prevision was 20/400 PHNH. At one week vision was 20/200 and at week two vision was 20/100−. Even at week one, patient noticed a marked increase in vision. At week two, vision was 20/100 (slow) near vision 20/70.

Patient 19: This patient was phakic and diagnosed as suffering from mild dry AMD right<left. Prevision was 20/20−1 right 20/25−3 PHNH left. At one week left remained at 20/25−3 but at two weeks vision was 20/20−1 left.

Patient 20: This patient was pseudophakic and diagnosed as suffering from dry AMD right<left. Prevision was 20/25−1,+1 right and 20/25−3 left, PHNH. At one week left eye was 20/25 and as strong as the right eye. At week two vision was 20/20−1 and stronger than the right. At four weeks both eyes were treated and vision was 20/20 right 20/20 left.

Patient 21: This patient was phakic and diagnosed as suffering from Lebers Congenital Amaurosis. Prevision was 20/CF or 6'/400 PHNH right, LP (light perception) left. At one week s vision was 6'/100 right and HM (hand motion). At week two, vision improved to 20/400 right, HM left. At week three, vision improved to 20/200−1 right, and remained at HM left. At six weeks vision was 20/200 with a near vision 20/70.

Patient 22: This patient was phakic and diagnosed as suffering from diabetic retinopathy. Prevision was 20/200 right and 20/200 slow left eye PHNH. The weaker of the two eyes or left eye was treated. At one week vision was 20/200 right 20/100−1 left. At week three both eyes were treated and vision was 20/100 right, 20/100 left.

Patient 23: This patient was pseudophakic and diagnosed as suffering from AMD and is status post visudyne laser. Prevision was HM hand motion. On the first day vision was 1'/400 and at one week 1'/100 and he reports a significant improvement of peripheral vision. At week three vision was 8'/400.

Patient 24: This patient was pseudophakic and diagnosed as suffering from dry AMD with prevision 20/40+PHNH. At two weeks vision was 20/25. At two months the patient stopped meds and vision was 20/40. At 10 weeks vision returned to 20/25.

Patient 25: This patient was pseudophakic and diagnosed as suffering from dry AMD and occult wet AMD with prevision of 20/30+ PHNH. At one day vision was 20/20− and this has remained through 2 months.

Patient 26: This patient was pseudophakic and diagnosed as suffering from dry AMD with prevision of 20/30−1 +3 PHNH. At one day vision was 20/20−2 +3.

Patient 27: This patient was pseudophakic and diagnosed as suffering from pre retinal fibrosis with a prevision 20/40− PHNH. At one day vision was 20/40+ and at one week 20/25−2.

Patient 28: This patient was phakic and diagnosed as suffering from macular hole right eye and mild dry AMD and early cataract left. Previson was CF 10/400 PHNH with near 20/400+ right and 20/30 PHNH. Near 20/25 left. Medication was applied to the right only. At day one vision was 20/400 right with near vision 20/100 in the right eye. The left eye improved to 20/20− at distance and 20/20 at near.

Patient 29: This patient was pseudophakic and diagnosed as suffering from dry AMD right<left. The left eye has aniridia (NO IRIS). Prevision was 20/30−1 PHNH no help right eye and 20/100− PH 20/70−1 left eye and a near vision of 20/70 left. The left eye was treated first initially. At one week vision was 20/70− and at 4-wks 20/70. Both eyes were treated and at two months vision was 20/25 right and 20/50 left. Near vision left improved to 20/30.

While this invention has been described with reference to specific embodiments, those of ordinary skill in the art will understand that variations in these methods and compositions may be used and that it is intended that the invention may be practiced otherwise than as specifically described herein. Accordingly, this invention includes all modifications encompassed within the spirit and scope of the invention as defined by the claims.

What is claimed is:

1. A method of treating a human eye disease, the method comprising topically administering to an eye affected with the disease, an amount of a composition consisting essentially of an acetylcholine esterase inhibitor sufficient to provide a therapeutic benefit, wherein the eye disease is age related macular degeneration, macular cyst, macular hole, solar retinopathy, diabetic retinopathy, branch retinal vein occlusion, or Lebers Congenital Amaurosis.

2. The method of claim 1, wherein the composition is administered at bedtime.

3. The method of claim 2, wherein said inhibitor is (2-mercaptoethyl) trimethylammonium iodide O,O-diethyl phosphorothioate.

4. The method of claim 3, wherein said (2-mercaptoethyl) trimethylammonium iodide O,O-diethyl phosphorothioate is present at a concentration of 0.001% to 0.25%.

5. The method of claim 4, wherein the concentration of (2-mercaptoethyl) trimethylammonium iodide O,O-diethyl phosphorothioate is 0.0075%.

6. The method of claim 4, wherein the concentration of (2-mercaptoethyl) trimethylammonium iodide O,O-diethyl phosphorothioate is 0.03%.

7. The method of claim 4, wherein the concentration of (2-mercaptoethyl) trimethylammonium iodide O,O-diethyl phosphorothioate is 0.12%.

8. The method of claim 2, wherein the acetylcholine esterase inhibitor is contained in a pharmaceutically acceptable carrier buffer solution.

9. The method of claim 2, wherein the eye disease is age related macular degeneration.

10. The method of claim 2, wherein the eye disease is diabetic retinopathy.

11. A method of treating an eye disease of a patient which comprises topically administering to an eye affected with the disease, an amount of a composition consisting essentially of (2-mercaptoethyl) trimethylammonium iodide O,O-diethyl phosphorothioate sufficient to provide a therapeutic benefit, wherein the eye disease is age related macular degeneration, macular cyst, macular hole, solar retinopathy, diabetic retinopathy, branch retinal vein occlusion, or Lebers Congenital Amaurosis and wherein the composition has (2-mercaptoethyl) trimethylammonium iodide O,O-diethyl phosphorothioate content of 0.001% to about 0.25%.

12. The method of claim 11, wherein the composition is administered at bedtime.

13. The method of claim 12, wherein the composition has (2-mercaptoethyl) trimethylammonium iodide O,O-diethyl phosphorothioate content of up to about 0.12%.

14. The method of claim 13, wherein said (2-mercaptoethyl) trimethylammonium iodide O,O-diethyl phosphorothioate is present at a concentration of 0.001%.

15. The method of claim 13, wherein the concentration of (2-mercaptoethyl) trimethylammonium iodide O,O-diethyl phosphorothioate is about 0.0075%.

16. The method of claim 13, wherein the concentration of (2-mercaptoethyl) trimethylammonium iodide O,O-diethyl phosphorothioate is about 0.03%.

17. The method of claim 13, wherein the concentration of (2-mercaptoethyl) trimethylammonium iodide O,O-diethyl phosphorothioate is about 0.12%.

18. The method of claim 11, wherein the acetylcholine esterase inhibitor is contained in a pharmaceutically acceptable buffer solution.

19. The method of claim 11, wherein the eye disease is age related macular degeneration.

20. The method of claim 11, wherein the eye disease is diabetic retinopathy.

21. A method of treating an eye disease of a patient which comprises topically administering to an eye affected with the disease, an amount of a composition consisting essentially of (2-mercaptoethyl) trimethylammonium iodide O,O-diethyl phosphorothioate sufficient to provide a therapeutic benefit, wherein the eye disease is age related macular degeneration, macular cyst, macular hole, solar retinopathy, diabetic retinopathy, branch retinal vein occlusion, or Lebers Congenital Amaurosis and wherein the composition has (2-mercaptoethyl) trimethylammonium iodide O,O-diethyl phosphorothioate content of about 0.03%.

22. The method of claim 21, wherein the composition is administered at bedtime.

23. The method of claim 22, wherein the eye disease is age related macular degeneration.

24. The method of claim 22, wherein the eye disease is macular cyst.

25. The method of claim 22, wherein the eye disease macular hole.

26. The method of claim 22, wherein the eye disease is solar retinopathy.

27. The method of claim 22, wherein the eye disease is diabetic retinopathy.

28. The method of claim 22, wherein the eye disease is branch retinal vein occlusion.

29. The method of claim 22, wherein the eye disease is Lebers Congenital Amaurosis.

30. The method of claim 22, wherein the acetylcholine esterase inhibitor is contained in pharmaceutically acceptable carrier buffer solution.

31. A method of treating a disease or disorder of the posterior region of the eye, the method comprising topically administering to the eye, an amount of a composition consisting essentially of (2-mercaptoethyl) trimethylammonium iodide O,O-diethyl phosphorothioate sufficient to provide a therapeutic benefit to alleviate the diminished visual acuity in the human patient, wherein the composition has (2-mercaptoethyl) trimethylammonium iodide O,O-diethyl phosphorothioate content of about 0.03% wherein said composition is administered at bedtime.

32. The method of claim 31, wherein the disease or disorder of the posterior region of the eye is age related macular degeneration, macular cyst, macular hole, solar retinopathy, diabetic retinopathy, branch retinal vein occlusion, or Lebers Congenital Amaurosis.

33. A method of treating a human patient suffering from an eye disease, the method comprising topically administering to the eye affected with the disease, a composition consisting essentially of an amount of (2-mercaptoethyl) trimethylammonium iodide O,O-diethyl phosphorothioate sufficient to provide a therapeutic benefit, wherein the eye disease is age related macular degeneration, macular cyst, macular hole, solar retinopathy, diabetic retinopathy, branch retinal vein occlusion, or Lebers Congenital Amaurosis and wherein the composition has (2-mercaptoethyl) trimethylammonium iodide O,O-diethyl phosphorothioate content of about 0.03% and wherein said composition administered at bedtime.

34. The method of claim 6, wherein the eye disease is age related macular degeneration.

35. The method of claim 6, wherein the eye disease is macular cyst.

36. The method of claim 6, wherein the eye disease macular hole.

37. The method of claim 6, wherein the eye disease is solar retinopathy.

38. The method of claim 6, wherein the eye disease is diabetic retinopathy.

39. The method of claim 6, wherein the eye disease is branch retinal vein occlusion.

40. The method of claim 6, wherein the eye disease is Lebers Congenital Amaurosis.

41. The method of claim 13, wherein the eye disease is age related macular degeneration.

42. The method of claim 13, wherein the eye disease is macular cyst.

43. The method of claim 13, wherein the eye disease macular hole.

44. The method of claim 13, wherein the eye disease is solar retinopathy.

45. The method of claim 13, wherein the eye disease is diabetic retinopathy.

46. The method of claim 13, wherein the eye disease is branch retinal vein occlusion.

47. The method of claim 13, wherein the eye disease is Lebers Congenital Amaurosis.

* * * * *